United States Patent [19]

Clecak et al.

[11] Patent Number: 4,522,911

[45] Date of Patent: Jun. 11, 1985

[54] DEEP ULTRA-VIOLET LITHOGRAPHIC RESISTS WITH DIAZOHOMOTETRAMIC ACID COMPOUNDS

[75] Inventors: Nicholas J. Clecak; Dennis R. McKean; Robert D. Miller, all of San Jose; Terry C. Tompkins, Los Altos; Carlton G. Willson, San Jose, all of Calif.

[73] Assignee: International Business Machines Corporation, Armonk, N.Y.

[21] Appl. No.: 508,642

[22] Filed: Jun. 28, 1983

[51] Int. Cl.³ .................... G03C 1/54; G03C 1/60; C07C 113/00
[52] U.S. Cl. .................... 430/192; 430/170; 430/193; 430/326; 534/560
[58] Field of Search .............. 430/192, 170, 193; 260/141 D

[56] References Cited

U.S. PATENT DOCUMENTS

| | | | |
|---|---|---|---|
| 3,567,451 | 3/1971 | Borden et al. | 430/193 |
| 3,567,453 | 3/1971 | Borden | 430/193 |
| 3,573,917 | 4/1971 | Okamoto | 430/193 |
| 4,207,107 | 6/1980 | Ross | 430/193 |
| 4,284,706 | 8/1981 | Clecak et al. | 430/193 |
| 4,339,522 | 7/1982 | Balanson et al. | 430/192 |

OTHER PUBLICATIONS

Current Abstracts, vol. 66, No. 2, Issue 710, #258014, 7-1977.
Grant, B. D., "Deep UV Photoresists I. Meldrum's Diazo Sensitizer", IEEE Transactions on Electron Devices, vol. ed. 28, No. 11, pp. 1300-1305.

*Primary Examiner*—Charles L. Bowers, Jr.
*Attorney, Agent, or Firm*—Joseph G. Walsh

[57] ABSTRACT

A lithographic resist for use with deep ultra-violet radiation comprising an acidic resin and a diazohomotetramic acid sensitizer.

7 Claims, No Drawings

DEEP ULTRA-VIOLET LITHOGRAPHIC RESISTS WITH DIAZOHOMOTETRAMIC ACID COMPOUNDS

DESCRIPTION

1. Technical Field

The present invention deals with lithographic resists for use with deep ultra-violet light, i.e. light below 300 nm. In particular, it deals with such resists comprising an acidic resin and a specific type of sensitizer.

2. Background Art

U.S. Pat. No. 4,339,522 discloses the use of certain Meldrum's diazo compounds as sensitizers for deep ultraviolet when incorporated in resins. While such compositions have been used with success, difficulties are encountered in their commercial use. Such materials which are adequately soluble in the casting mixtures are also lost to a significant extent by volatilization during the prebake step. This is a major concern, as it is a source of large process variability. In this respect, the wafer to wafer variability has been correlated with the loss of sensitizer observed spectroscopically. This feature is definitely disadvantageous for any commercial resist formulation and no compound fully satisfies both the solubility and thermal stability criteria.

DESCRIPTION OF THE INVENTION

According to the present invention, lithographic resists for use with deep ultra-violet light comprise an acidic resin and a sensitizer which is a diazohomotetramic acid compound. It has been determined spectroscopically that these sensitizers are completely stable to the normal prebake conditions. The desirable sensitizer properties of solubility and spectral matching at 254 nm are also obtained with these compounds.

The following formulas illustrate the structures of some of the diazohomotetraminic acid compounds useful in the present invention.

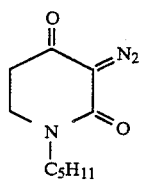

I

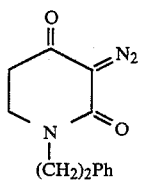

II

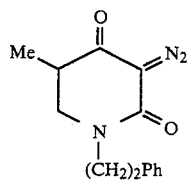

III

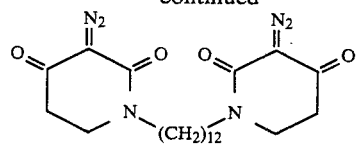

IV

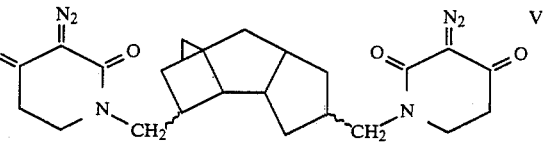

V

As may be seen by inspection of the above formulas, what is required for use as a sensitizer in the present invention is the presence of the structure

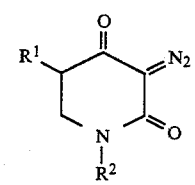

where $R^1$ is hydrogen or an alkyl group and $R^2$ is an alkyl group, an arylalkyl group, or a bifunctional group linking two of the rings together. These compounds are described in the present application as diazohomotetramic acid compounds, since they all share this structure. All of these materials are soluble in common casting solvents and are not volatilized during prebake. The bifunctional derivatives 4 and 5 are of particular interest not only because of their strong absorption at 254 nm, but also because they are very high contrast sensitizers a maximum polarity change attending photochemical decomposition. It should be noted that derivatives of diazohomotetramic acid, unlike Meldrum's diazo, produce photostable ketenes when irradiated at 254 nm. In this regard, the irradiation of 2 incorporated in novolac resin at 77° K. produces the expected ketene derivatives which is stable at −78° C. (IR) in vacuum but disappears rapidly when moist air is admitted into the chamber.

For use in the present invention the resist formulation includes the diazomomotetramic acid sensitizers and an acidic resin. Many such resins are well known in the art. They include, for example, novolac resins such as p-cresol novolac, poly(p-hydroxystyrene) and copolymers of methacrylic acid with esters thereof. The sensitizer is in admixture with the resin, and present in a quantity such that upon exposure of the resist to deep ultra-violet radiation the composition becomes more soluble in alkaline developer. In general, the sensitizer is present in from about 5 to 50% of the weight of the resin.

A solution of 4 (0.9 g in 29.1 g of a 30% solution of cresol novolac in diglyme) produced high quality films of ~0.8 μm thickness when spun at 3000 RPM. No loss of sensitizer was observed upon baking these films (80°, 15 minutes) prior to exposure. A dose of only 20 mJ/cm² of DUV radiation produces a greatly enhanced dissolution rate in the exposed region. At 40 mJ/cm², the irradiated region is developed to substrate with little film loss from the unexposed portion using dilute KDH solution. This sensitivity is equal to or greater than that of common diazoquinone resists and of Meldrum's diazo resists.

The diazohomotetramic acid compounds of the present invention may be synthesized by a process which is useful as a general synthetic procedure to allow wide latitude with regard to substituent incorporation. The procedure also allows the preparation of bifunctional derivations from commercially available diamines. This synthetic procedure is outlined as follows:

Preparation of
1-1'-(Dodecamethylene)bis-N-N'-(methyl 2-aminopropanoate) (Compound 1)

A solution of 3.96 g of methyl acrylate, 4.60 g 1,12-dodecadiamine and 60 ml ethanol was stirred at 24° for 16 hours. The solvent was removed at reduced pressure to give 8.5 g of product.

Preparation of
1-1'-(Dodecamethylene)bis-N-N'-[N-(methoxy-carbonyl)ethyl ethyl malonamate] (Compound 2)

To a solution of 8.50 g compound 1 and 100 ml methylene chloride at 0° was added to solution of ethyl hydrogen malonate (6.03 g) in 25 ml methylene chloride followed by a solution of 9.62 g of dicyclohexyl carbodiimide in 25 ml methylene chloride. The resulting mexture was stirred 15 minutes at 0° and 16 hours at 24°. The reaction mixture was then filtered to remove the solid byproduct. The methylene chloride phase was washed with 50 ml water and 50 ml saturated sodium chloride solution and then dried over calcium sulfate. The solvent was removed at reduced pressure to give 12.85 g of compound 2.

Preparation of
1-1'-(Dodecamethylene)bis(3-methoxycarbonyl-2,4-piperidinedione) (Compound 3)

To a solution of 0.077 g sodium in 10 ml methanol at 24° under nitrogen was added a solution of 1.0 g of compound 2 in 20 ml toluene. The resulting solution was heated to reflux for 6 hours. The solvents were then removed at reduced pressure and the residue dissolved in 50 ml water. The aqueous solution was washed with 10 ml ether and then acidified with sulfuric acid, saturated with potassium chloride and extracted with three 25 ml portions of methylene chloride. The combined methylene chloride phase was dried over calcium sulfate and the solvent removed at reduced pressure to give 0.65 g of compound 3.

Preparation of
1-1'-(Dodecamethylene)bis(2,4-piperidinedione) (Compound 4)

A solution of 9.32 g of compound 3, 2.0 ml of 10% aqueous hydrochloric acid and 200 ml of acetonitrile was heated to reflux for 2 hours. The volatile materials were removed at reduced pressure to give 6.80 g of compound 4.

Preparation of
1-1'-(Dodecamethylene)bis(3-diazo-2,4-piperidinedione) (Compound 5)

To a solution of 5.75 g of compound 4 and 400 ml acetonitrile at 0° under nitrogen was added a solution of 7.29 g tosyl azide in 10 ml acetonitrile followed by a solution of 3.57 g triethylamine in 10 ml acetonitrile. The resulting solution was stirred 15 minutes at 0° and 4 hours at 24°. Acetonitrile was removed at reduced pressure and the residue dissolved in 200 ml methylene chloride. The methylene chloride phase was washed with 50 ml of 5% sodium hydroxide solution, 50 ml of water and 50 ml of saturated sodium chloride solution. The methylene chloride phase was then dried over magnesium sulfate and the solvent removed at reduced pressure. The crude product was then chromatographed on silica gel to give 3.08 g of compound 5.

We claim:

1. A lithographic resist composition for use with ultra-violet light of less than 300 nm wavelength, said composition comprising an acidic resin and in admixture therewith as a deep ultra-violet sensitizer a sufficient quantity of a diazohomotetramic acid compound having the formula

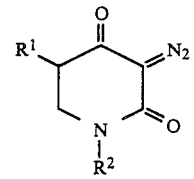

wherein $R^1$ is hydrogen or an alkyl group and $R^2$ is an arylalkyl group, an aryl group, or a bifunctional group linking two of the rings together,
   whereby upon exposure to deep ultra-violet radiation, the composition becomes more soluble in alkaline developer.

2. A lithographic resist composition as claimed in claim 1 wherein the sensitizer is

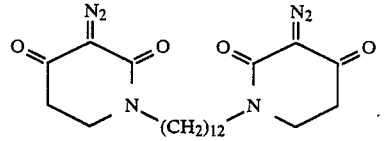

3. A lithographic resist composition as claimed in claim 1 wherein the sensitizer is

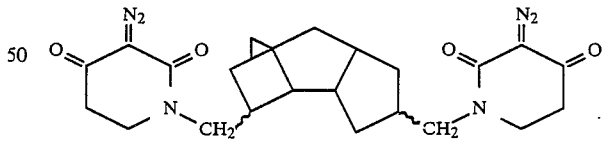

4. A lithographic resist composition as claimed in claim 1 wherein the resin is novolak.

5. A lithographic resist composition as claimed in claim 1 wherein the resin is p-cresol novolac.

6. A lithographic resist composition as claimed in claim 1 wherein the resin is p-hydroxystyrene.

7. A lithographic resist composition as claimed in claim 1 wherein the resin is methacrylic acid or a co-polymer thereof.

* * * * *

UNITED STATES PATENT AND TRADEMARK OFFICE
CERTIFICATE OF CORRECTION

PATENT NO. : 4,522,911

DATED : June 11, 1985

INVENTOR(S) : N. J. Clecak et al

It is certified that error appears in the above-identified patent and that said Letters Patent is hereby corrected as shown below:

Col. 4, line 31, "arylalkyl group, an aryl group" should read -- alkyl group, an arylalkyl group --.

Signed and Sealed this

Fifteenth Day of October 1985

[SEAL]

Attest:

DONALD J. QUIGG

Attesting Officer

Commissioner of Patents and
Trademarks—Designate